(12) United States Patent
Rein et al.

(10) Patent No.: US 8,017,365 B1
(45) Date of Patent: Sep. 13, 2011

(54) BIOGAS, FERTILIZER AND RECYCLABLE WATER PRODUCING SYSTEM

(76) Inventors: David A. Rein, Moorhead, MN (US); Patrick A. Rein, Moorhead, MN (US)

( * ) Notice: Subject to any disclaimer, the term of this patent is extended or adjusted under 35 U.S.C. 154(b) by 743 days.

(21) Appl. No.: 12/110,938

(22) Filed: Apr. 28, 2008

Related U.S. Application Data

(60) Provisional application No. 60/914,339, filed on Apr. 27, 2007.

(51) Int. Cl.
| | |
|---|---|
| C12P 7/06 | (2006.01) |
| C12P 7/08 | (2006.01) |
| C12P 7/14 | (2006.01) |
| C02F 11/04 | (2006.01) |
| C12M 1/02 | (2006.01) |

(52) U.S. Cl. ........ 435/161; 210/603; 210/609; 210/613; 210/615; 435/41; 435/162; 435/163; 435/253.6

(58) Field of Classification Search .................. None
See application file for complete search history.

(56) References Cited

U.S. PATENT DOCUMENTS

| | | | |
|---|---|---|---|
| 6,355,456 B1 | 3/2002 | Hallberg et al. | |
| 7,524,418 B2 * | 4/2009 | Hirl | 210/603 |
| 7,604,743 B2 * | 10/2009 | Hirl | 210/603 |
| 2008/0003654 A1 | 1/2008 | Hirl | |
| 2008/0176303 A1 * | 7/2008 | Massie | 435/163 |
| 2010/0041117 A1 * | 2/2010 | Hirl | 435/161 |

OTHER PUBLICATIONS

Morrison, E.M., A Digestible Idea, AG Innovation News, Apr.-Jun. 2008, 3 pgs, vol. 17, No. 2.
E3 Biofuels, The Basics of the Anaerobic Digestion Process, retrieved at <http://www.e3biofuels.com/basics.html> on Feb. 13, 2007, 1 pg.
Ethanol Producer Magazine, Easy to Digest, retrieved at <http://www.ethanolproducer.com/article-print.jsp?article_id=2071> on Feb. 13, 2007, 2 pgs.
Otter Tail Power Company, Make it Electric, Jan. 1, 2008, 3 pgs., vol. 21, No. 1.
Stowa, Struvite Recovery, retrieved at <http://www.stowa-selectedtechnologies.nl/Sheets/Sheets/Struvite.Recovery.html> on Feb. 13, 2007, 5 pgs.

* cited by examiner

*Primary Examiner* — Herbert J. Lilling
(74) *Attorney, Agent, or Firm* — Neustel Law Offices

(57) ABSTRACT

A resource production system using a byproduct from the production of ethanol for efficiently producing biogas and fertilizer from the byproducts of ethanol production. The resource production system using a byproduct of a production of ethanol generally includes a plurality of processes for producing an inorganic renewable fertilizer, such as struvite and a non-fossil fuel source of energy, such as biogas, by using various types of byproducts produced by the ethanol plant, such as but not limited to whole stillage, thin stillage and thin stillage solubles. The process also produces an organic fertilizer, such as biosolids and a liquid stream suitable for further processing to produce recyclable water at the ethanol plant.

17 Claims, 3 Drawing Sheets

BIOGAS, FERTILIZER AND RECYCLABLE WATER PRODUCING SYSTEM

CROSS REFERENCE TO RELATED APPLICATIONS

I hereby claim benefit under Title 35, United States Code, Section 119(e) of U.S. provisional patent application Ser. No. 60/914,339 filed Apr. 27, 2007. The 60/914,339 application is currently pending. The 60/914,339 application is hereby incorporated by reference into this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to ethanol production byproducts and more specifically it relates to a biogas, fertilizer and recyclable water producing system for efficiently producing biogas and fertilizer from the byproducts of ethanol production.

2. Description of the Related Art

Any discussion of the related art throughout the specification should in no way be considered as an admission that such related art is widely known or forms part of common general knowledge in the field.

Anaerobic digestion is a process in which microorganisms break down biodegradable material in the absence of oxygen. Anaerobic digestion is a renewable energy source because the process produces a methane and carbon dioxide rich biogas suitable for energy production helping to replace fossil fuels. The biogas is a natural-gas substitute that can be used in various applications, such as being burned in a furnace or used to power a turbine for electricity. Today, the process is widely used in wastewater treatment because it provides volume and mass reduction of the input material.

The production of ethanol generally requires a significant amount of fossil fuel to produce the product. For this reason, among others, the production of ethanol has been widely critized as to whether it is an efficient source of fuel, wherein the amount of energy required to produce ethanol may be close to the amount of energy outputted from the ethanol process. Because of the inherent problems with the related art, there is a need for a new and improved biogas, fertilizer and recyclable water producing system for efficiently producing biogas and fertilizer from the byproducts of ethanol production.

BRIEF SUMMARY OF THE INVENTION

The general purpose of the present invention is to provide a biogas, fertilizer and recyclable water producing system that has many of the advantages of the ethanol production byproducts mentioned heretofore. The invention generally relates to an ethanol production byproduct system including the steps of providing a byproduct from a production of ethanol, removing a volume of struvite from the byproduct and processing a remaining portion of the byproduct via anaerobic digestion, wherein the step of processing the remaining portion of the byproduct is performed after the step of removing the volume of struvite.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

An object is to provide a biogas, fertilizer and recyclable water producing system for efficiently producing biogas and fertilizer from the byproducts of ethanol production.

Another object is to provide a biogas, fertilizer and recyclable water producing system that reduces fossil fuel consumption.

An additional object is to provide a biogas, fertilizer and recyclable water producing system that increases profitability of ethanol production facilities.

An additional object is to provide a biogas, fertilizer and recyclable water producing system that removes the struvite from the liquid portion of the byproduct prior to the production of the biogas within the anaerobic digester.

A further object is to provide a biogas, fertilizer and recyclable water producing system that produces ethanol in an enhanced environmental manner by decreasing carbon emissions, by recycling various nutrients, such as magnesium, phosphorus and nitrogen into agricultural operations while conserving water in the processing plant.

Another object is to provide a biogas, fertilizer and recyclable water producing system that efficiently combines methane production with struvite production at an ethanol production facility.

Other objects and advantages of the present invention will become obvious to the reader and it is intended that these objects and advantages are within the scope of the present invention. To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview

Figure 1:
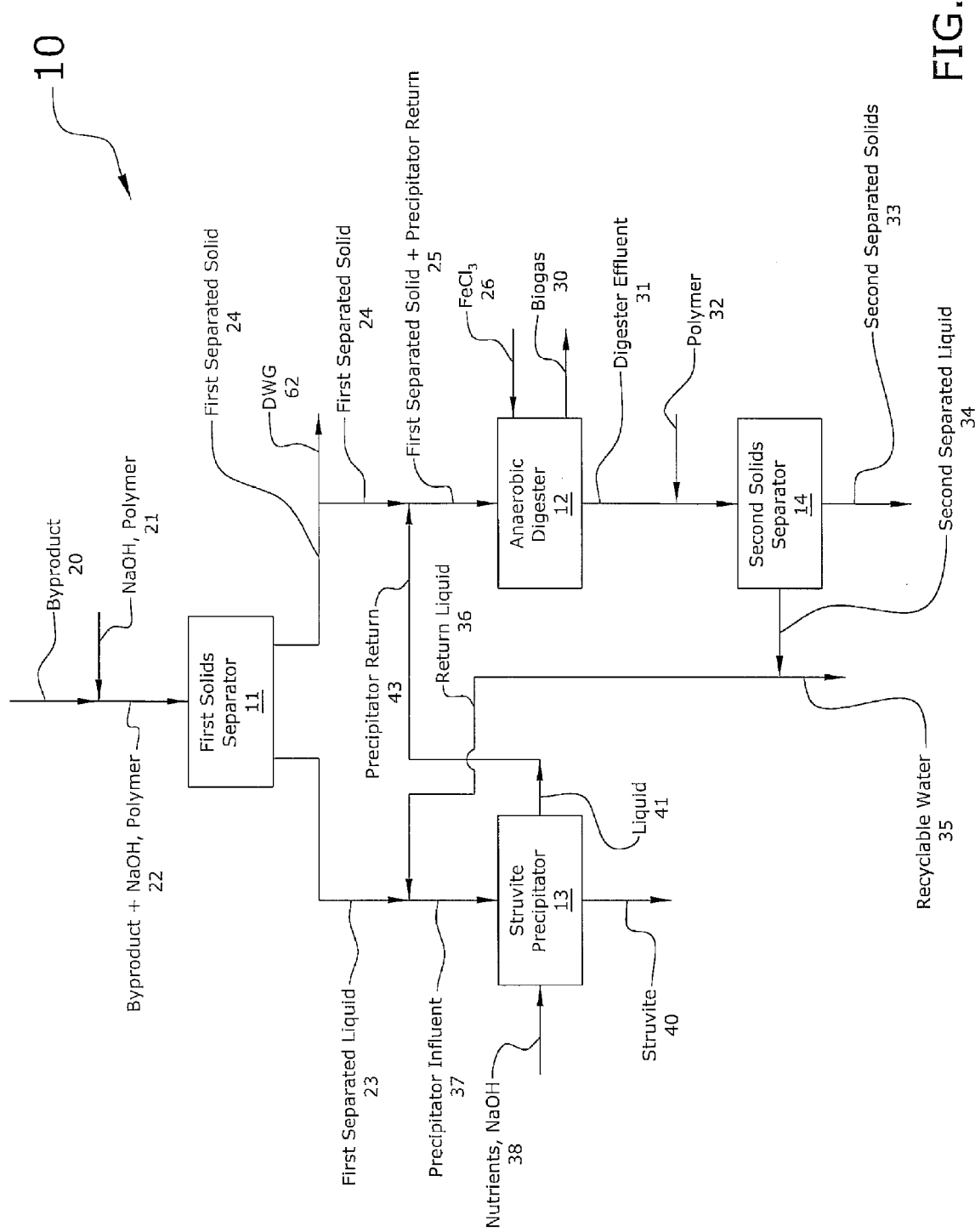
FIG. 1 is a flow diagram illustrating the process of the preferred embodiment to produce biogas, struvite, organic fertilizer solids and recyclable water from the byproducts of ethanol production.
Figure 2:
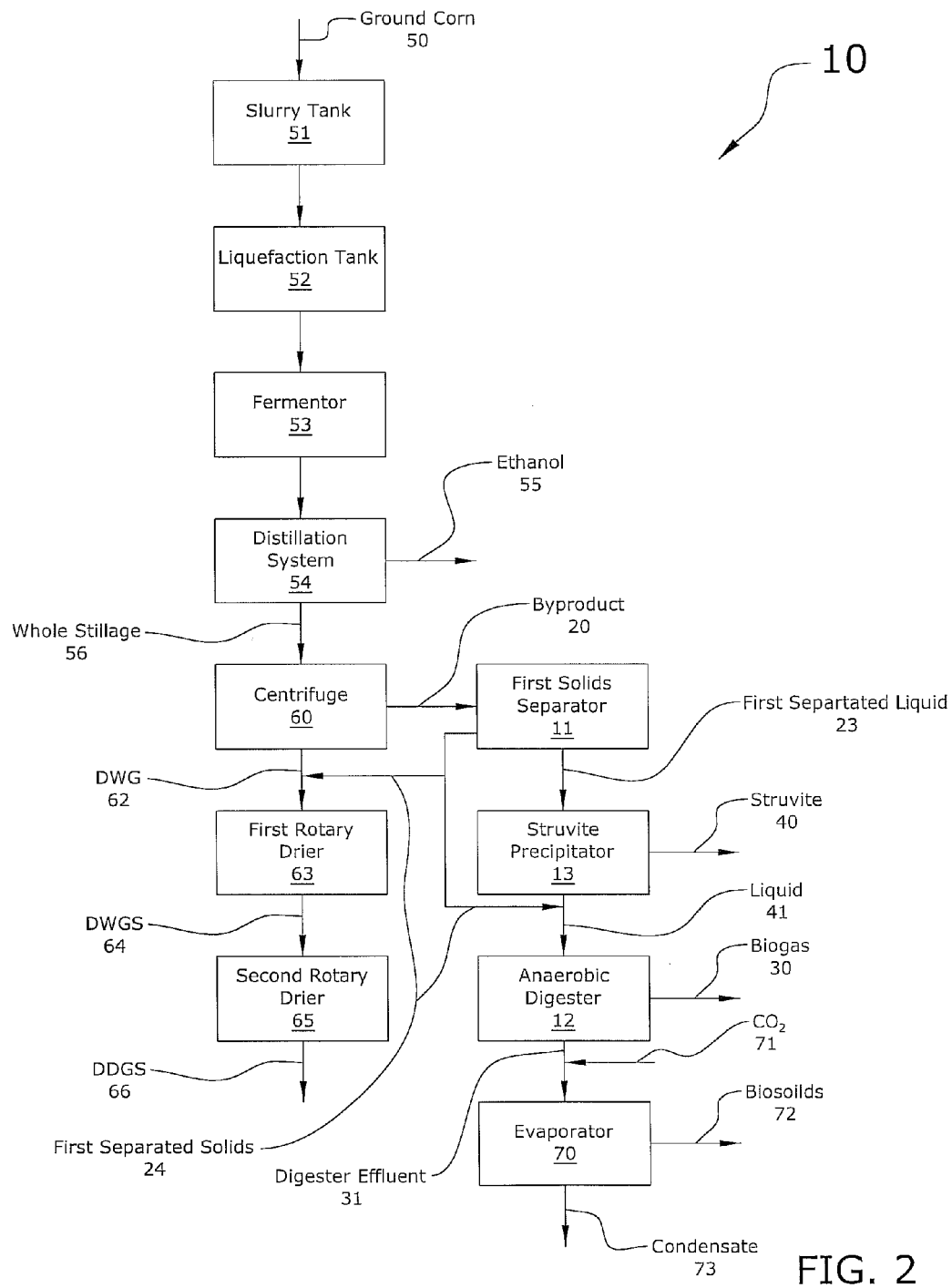
FIG. 2 is a flow diagram of a first embodiment of the present invention incorporated within an ethanol production facility.
Figure 3:
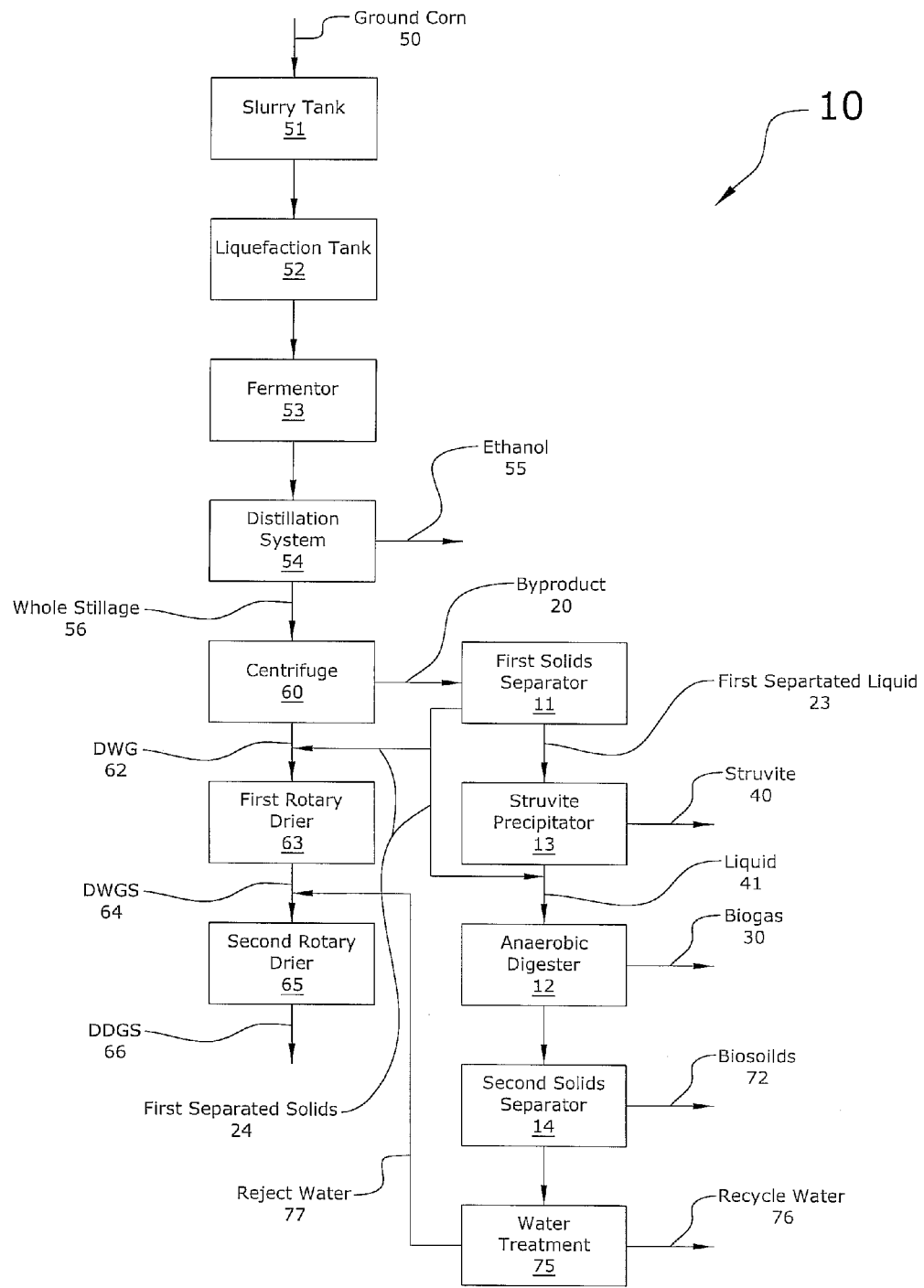
FIG. 3 is a flow diagram of a second embodiment of the present invention incorporated within an ethanol production facility.

Turning now descriptively to the drawings, in which similar reference characters denote similar elements throughout the several views, FIGS. 1 through 3 illustrates a biogas, fertilizer and recyclable water producing system 10, which comprises fermenting a ground corn 50, distilling the fermented corn 50 to produce ethanol 55 and whole stillage 56, centrifuging the whole stillage 56, producing a thin stillage 20 from the centrifuging step and processing the thin stillage 20 to produce struvite 40, biogas 30, second separated solids 33 (biosolids 72) and recyclable water 35.

The preferred embodiment utilizes a byproduct 20, such as but not limited to whole stillage, thin stillage or thin stillage solubles (i.e. thin stillage with the solids removed) from ethanol production as a feedstock to a solids separation process 11 to produce liquid stream 23 and solids stream 24. The liquid stream 23 becomes the primary feed stock for struvite precipitator 13 to form struvite 40, a renewable crystallized fertilizer. The liquid stream 41 from the struvite precipitator 13 becomes all or a portion of the feed stock for digester 12. The solids stream 24 from first solids separator 11 can be either recycled back to the DWG 62 (FIG. 2) to produce an enhanced protein feed or combined with the liquid stream 43 from the precipitator 13 to become the combined feed stock to digester 12 depending on prevailing local economic conditions.

Digester 12 produces biogas 30 (i.e. a mixture of methane, carbon dioxide and other minor constituents) and digester effluent 31, a semi liquid mixture of biosolids. Digester effluent 31 becomes the feed stock for solids separator 14. Solids separator 14 produces an organic fertilizer separated solids 33 (biosolids 72) and separated liquid 34. Separated liquid 34 (which is relatively high in buffering capacity and ammonia) can be used as return liquid 36 to the influent of struvite precipitator 13, used as feed stock to process 75 to produce recyclable water 76 or recycled back to the ethanol production process through evaporator 70 to form condensate 73.

The present invention forms inorganic struvite fertilizer 40, biogas 30, organic fertilizer separated solids 33 (or biosolids 72) and recyclable water 35 (73). The inorganic fertilizer 40 produced is comprised primarily of struvite. It is appreciated that the fertilizer substances 33, 72, 40, recyclable water 35 (73) and biogas 30 may be produced utilizing various processes, all which utilize the byproducts 20 from the ethanol production process. The present invention may utilize various byproducts 20 and/or a combination of 20 and 62 from the production of ethanol. Some examples of byproducts 20 that may be utilized are whole stillage, thin stillage, thin stillage soluble and/or thick stillage (i.e. syrup).

B. Solids Separators

The preferred embodiment includes a first solids separator 11 and a second solids separator 14. The first solids separator 11 and the second solids separator 14 are utilized at different stages in the process of producing biogas, fertilizer and recyclable water from the byproducts 20 of the production of ethanol. The solids separators are capable of separating a large percentage of the water from a liquid stream to thus produce a generally solids-free filtrate and a protein rich solids stream. In the preferred embodiment a plate-and-frame filter press is utilized as the first solids separator 11.

An important aspect of the first solids separator 11 is to transfer most of the magnesium, ammonia and phosphorus into the liquid stream 23 from the byproduct stream 20. The solids separator 11 may be comprised of screw presses, belt filter presses or centrifuges. A high degree of struvite removal prevents struvite scaling and accumulation in the anaeorbic digester(s). The first solids separator 11 preferably squeezes out enough water to produce approximately 35% solids filter cake and also captures approximately 98% of the influent solids. It is appreciated that first solids separator 11 could be a two-step solids separator designed to optimize (i.e., minimize the use of NaOH) and remove a majority of the oil from the liquid going forward as first separated liquid 23. The second step of the separation is accomplished by adding NaOH to bring the pH up to approximately 6. At this pH the oil/fat naturally separate from the liquid stream. This oil/fat layer can be separated via an underflow weir or other density separator.

The second solids separator 14 is utilized to dewater the anerobic digester effluent 31 to produce second separated solids 33 (or 72) and separated liquid 34. A solids capture of approximately 85% and a cake solids concentration of approximately 15 to 20% have been specified for the second solids separator 14. The second solids separator 14 may be comprised of a belt filter press in order to satisfy the preferred requirements of solids capture of approximately 85% and cake solids concentration of approximately 15%.

Another option rather than the second solids separator 14 is to utilize an existing or new ethanol plant evaporator 70 to produce the biosolids 72 and condensate water 73 as illustrated in FIG. 2. The use of the evaporator 70 may also be beneficial for thickening the biosolids 72. The biosolids 72 could also be sent directly to the first rotary drier 63 as an additive to the DWG 62. The need for capital expenditures for recycle or reuse water equipment may also be eliminated or reduced because condensate 73 from the evaporator 70 will be generated and reused.

C. Struvite Precipitator

The preferred embodiment includes a struvite precipitator 13 to receive a first liquid 23 from the first solids separator 11 and possibly water 36 from the second solids separator 14. The first liquid 23 and the water 36 combine to produce a precipitator influent 37. Nutrients and NaOH (38) are added to drive the precipitation reaction. The constituents (i.e. magnesium, ammonium, phosphate, and trace amounts of other inorganic constituents) of the precipitator influent 37 is preferably crystallized within the struvite precipitator 13 to produce a water substance 41 and a crystallized fertilizer substance 40 (struvite plus small amounts of other inorganics).

Struvite crystals (Magnesium Ammonium Phosphate) are created in the struvite precipitator 13. The struvite precipitator 13 removes large amounts of phosphorus, magnesium and some nitrogen from the precipitator influent stream 37, wherein the products from the precipitator 13 are supernatant liquid 41 and the crystallized struvite 40. The struvite precipitator 13 processes the byproduct 20 prior to the anaerobic digester 12 to remove a volume of struvite from the byproduct 20. It is appreciated that if the struvite is not removed prior to anaerobic digestion, the struvite forms in the anaerobic digester 12 and will be difficult to remove because the struvite will be co-mingled in the solids 33. Removing the struvite beforehand also reduces digester 12 operation problems, such as scaling or accumulating in the digester 12 (thus reducing the active tank volume). In many cases, struvite scale is a significant operational difficulty in anaerobic digesters 12 as well as their mixing systems, discharge piping, and subsequent solids separation equipment. Removing the struvite prior to anaerobic digestion also helps in maintaining a low level of phosphorus so as to not over apply phosphorus to the land when utilizing the biosolids from solids separator 14 (i.e. separated solids 33 or biosolids 72) as fertilizer.

D. Anaerobic Digester

The preferred embodiment includes at least one anaerobic digester 12 to fluidly receive a mixture of solids 24 from the first solids separator 11 and precipitator return 43 from the struvite precipitator 13. If insufficient magnesium, ammonium, and phosphate have been removed from stream 41 in the struvite precipitator 13 to prevent struvite precipitation in the anaerobic digester 12, iron salts 26 such as ferric chloride or ferrous chloride may be added to the anaerobic digesters to help control struvite precipitation in the anaerobic digester. The anaerobic digester 12 also fluidly transmits a produced digester effluent 31 to the second solids separator 14. The anaerobic digester 12 is utilized to produce the biogas 30 and the digester effluent 31 in the preferred embodiment. Any byproduct 20 not sent to the struvite precipitator 13 from the first solids separator 11 is subsequently fed into one or more anaerobic digesters 12. The anaerobic digester 12 may be comprised of anaerobic digesters 12 capable of thermophilic or mesophilic processes. The anaerobic digester 12 may or may not receive a remaining portion of solids 24 from the byproduct 20 depending on local mark conditions and also receives a precipitator return 43 from the struvite precipitator 13 in producing the biogas 30.

A majority of the organic byproducts 20 fed to the anaerobic digester 12 are subsequently converted to biogas 30. The biogas 30 may be comprised of various substances, such as but not limited to methane. The biogas 30 may subsequently be stored for later use or recirculated to be utilized directly within the ethanol production process to displace the use of other energy sources, such as natural gas, coal or electricity. It is appreciated that the anaerobic step 12 takes place after the struvite precipitator step 13.

E. Detailed Operation of Preferred Embodiment

As illustrated in FIG. 1, the process of the preferred embodiment is as follows. It is appreciated that the process may be varied according to specific design constraints or to accommodate for alterations in respective amounts of the desired product. The preferred embodiment utilizes a byproduct 20 (e.g. whole stillage, thin stillage, soluble thin stillage, thick stillage, etc.) from the production of ethanol 55. It is appreciated that the Ostara process may also be utilized for the struvite precipitator 13. Once the byproduct 20 is received, the byproduct 20 is combined with stream 21, wherein stream includes pH adjustment with a chemical such as a sodium hydroxide (NaOH) and polymer for improved solids separation. The combined stream 20 and stream 21 form stream 22 which is fed to the first solids separator 11.

The output streams from the solids separator 11 are separated liquid stream 23 and first separated solid 24. The separated liquid stream 23 and or returned liquid 36 are combined to form the precipitator influent stream 37 and directed to the struvite precipitator 13. The precipitator influent 37 inorganic constituents are preferably crystallized to produce a fertilizer substance (struvite plus small amounts of other inorganic substance). The effluent streams from precipitator 13 are a liquid substance 41 and a fertilizer substance 40.

Sodium Hydroxide (NaOH) or other pH raising chemical and nutrients are fed from stream 38 to the struvite precipitator 13 to produce both struvite in stream 40 and liquid in stream 41. Struvite (Magnesium Ammonium Phosphate plus small amounts of other crystallized inorganics) crystals 40 are subsequently created in the struvite precipitator 13 from the precipitator influent 37. The struvite precipitator 13 also preferably removes large amounts of magnesium, phosphorus and some nitrogen, wherein the products from the precipitator 13 are liquid 41 and the crystallized struvite 40. Liquid 41 becomes precipitator return 43.

The struvite 40 may be collected and utilized for various purposes, such as but not limited to being reused in the fertilizer applications. Struvite is a slow release, renewable fertilizer that commonly sells into the turf market at a premium price. The liquid 41 is comprised of precipitator discharge and becomes precipitator return 43 and is combined with separated solids of stream 24 and fed to anaerobic digester 12. The fertilizer substance 40 may be utilized for various purposes, such as but not limited to fertilizing the corn utilized to produce the ethanol 55.

Any byproduct 20 not sent to the struvite precipitator 13 from the first solids separator 11 can be fed into one or more anaerobic digesters 12 as a semisolid in stream 24. Stream 24 can be added to DWG 62 to enhance DWG 62 protein content or to anaerobic digester 12 depending on local market conditions of DWG 62 and natural gas. The solids in stream 24 are also combined with a precipitator return from stream 43 to produce stream 25 to feed to the anaerobic digester 12. All or a portion of the first solids 24 can also be sent to DWG 62. The liquid 41 is either fed alone or in combination with the first separated solid 24 and becomes stream 25.

Iron salts, such as, ferric chloride or ferrous chloride ($FeCl_3$ or $FeCl_2$) and iron salts from stream 26 is fed to the anaerobic digester 12 along with stream 25 to produce both biogas in stream 30 and digester effluent in stream 31. The ferric chloride 26 may be utilized to forestall the struvite precipitation in the digesters 12 and appurtenances. A small amount of ferric chloride 26 may eliminate remaining potential struvite scaling in the anaerobic digester 12. The biogas 30 may subsequently be stored for later use or recirculated to be utilized directly within the ethanol production process to displace the use of other energy sources.

A portion of the byproducts 20 (that are not converted to biogas 30) are subsequently fed into another solids separation process. The portion of byproduct (i.e. digester effluent 31) is comprised of microorganisms and other solid particles. The digester effluent 31 produced from the anaerobic digester 12 is directed toward the second solids separator 14 (or evaporator 70 shown in FIG. 2) and also combined within a polymer stream 32 to improve solids separation. The microorganisms and other solids 33 (or 72) are separated from the liquid portion 34 within the second solids separation process 14.

The second solids separator 14 produces a second separated solids 33 (or 72) and a liquid stream 34. Stream 33 (or 72) can be utilized as biosolids fertilizer or added back to DWG 62. A first portion of the liquid 34 is collected as recyclable water 35 and a second portion of the liquid can be fed to the first separated liquid stream 23 as the return liquid 36 for buffering and ammonium addition. It is appreciated that the above process may adjust the quantities of the biogas 30, fertilizer 40, water 35, second separated solids 33 (72)

enhanced protein feed (first separated solids 24 sent to DWG 62) produced according to current needs.

F. Overview of Preferred Embodiment Integrated with an Ethanol Plant

The present invention discloses examples of possible embodiments of the present invention when connected to an ethanol production facility. A first embodiment is illustrated in FIG. 2 and a second embodiment is illustrated in FIG. 3. The first embodiment focuses around an evaporator 70 and the second embodiment focuses around a water treatment system 75.

Both the first embodiment and the second embodiment include a general process of receiving ground corn 50 by a slurry tank 51, processing the ground corn 50 within the slurry tank 51 and transferring to a liquefaction unit 52. The resultant is then transferred to a fermentor 53 and then to a distillation system 54, wherein ethanol 55 and whole stillage 56 are produced. The ethanol 55 is collected for sale and use as an alternate fuel source. The whole stillage 56 is preferably comprised of approximately 88% $H_2O$.

The whole stillage 56 is directed to a centrifuge 60, wherein thin stillage 20 (comprised of approximately 94% $H_2O$) and DWG 62 (distiller's wet grains) are produced. The enhanced protein feed (first separated solids 24) can be added to the DWG 62 or sent to the anaerobic digester 12. The DWG 62 is preferably comprised 60%-65% $H_2O$. The DWG 62 can be marketed as water material or sent to a first rotary drier 63 to produce DWGS 64 (distiller's wet grain with solubles) which is approximately 30% $H_2O$ and then to a second rotary drier 65 to produce DDGS 66 (distiller's dry grain with solubles) which is approximately 10%-12% $H_2O$.

The thin stillage 20 is directed to the first solids separator 11 and a similar process as described in Section E (Detailed Operation of Preferred Embodiment) is performed upon the thin stillage 20. $CO_2$ 71 (carbon dioxide) may also be added to the digester effluent 31 from the anaerobic digester 12 which in turn is directed to the evaporator 70 to control scaling. The evaporator 70 then produces biosolids 72 (40% solids) and condensate 73 (i.e. recyclable water). Alternately, instead of the evaporator 70, the recyclable water 35 from the second solids separator 14 may be run directly back into slurry tank 51 or ran through a water treatment process 75 to produce both purified recycled water 76 and reject water 77. The reject water 77 may then be combined with the DWGS 64 to enter into the second rotary drier 65.

What has been described and illustrated herein is a preferred embodiment of the invention along with some of its variations. The terms, descriptions and figures used herein are set forth by way of illustration only and are not meant as limitations. Those skilled in the art will recognize that many variations are possible within the spirit and scope of the invention, which is intended to be defined by the following claims (and their equivalents) in which all terms are meant in their broadest reasonable sense unless otherwise indicated. Any headings utilized within the description are for convenience only and have no legal or limiting effect.

We claim:

1. A method of using a byproduct from a production of ethanol, comprising:
   providing a byproduct from a production of ethanol;
   removing a volume of struvite from said byproduct; and
   processing a remaining portion of said byproduct via anaerobic digestion, wherein said step of processing said remaining portion of said byproduct is performed after said step of removing said volume of struvite.

2. The method of using a byproduct from a production of ethanol of claim 1, including a step of separating a liquid portion from said byproduct prior to said removing step, wherein said struvite is removed from said liquid portion.

3. The method of using a byproduct from a production of ethanol of claim 1, including a struvite precipitator adapted to remove said volume of said struvite.

4. The method of using a byproduct from a production of ethanol of claim 1, including a step of separating a biosolid from a digester effluent of said anaerobic digestion step.

5. The method of using a byproduct from a production of ethanol of claim 1, including a step of separating a liquid portion from a digester effluent of said anaerobic digestion step.

6. The method of using a byproduct from a production of ethanol of claim 5, including a step of reusing said liquid portion as recyclable water.

7. The method of using a byproduct from a production of ethanol of claim 1, wherein said byproduct is comprised of thin stillage.

8. The method of using a byproduct from a production of ethanol of claim 1, wherein said byproduct is comprised of whole stillage.

9. The method of using a byproduct from a production of ethanol of claim 1, wherein said byproduct is comprised of thin stillage solubles.

10. A method of using a byproduct from a production of ethanol, comprising:
    providing a byproduct from a production of ethanol;
    separating a liquid portion from said byproduct;
    removing a volume of struvite from said liquid portion; and
    processing a remaining portion of said byproduct via anaerobic digestion, wherein said step of processing said remaining portion of said byproduct is performed after said step of removing said volume of struvite.

11. The method of using a byproduct from a production of ethanol of claim 10, including a struvite precipitator adapted to remove said volume of said struvite.

12. The method of using a byproduct from a production of ethanol of claim 10, including a step of separating a biosolid from a digester effluent of said anaerobic digestion step.

13. The method of using a byproduct from a production of ethanol of claim 10, including a step of separating a liquid portion from a digester effluent of said anaerobic digestion step.

14. The method of using a byproduct from a production of ethanol of claim 13, including a step of reusing said liquid portion as recyclable water.

15. The method of using a byproduct from a production of ethanol of claim 10, wherein said byproduct is comprised of thin stillage.

16. The method of using a byproduct from a production of ethanol of claim 10, wherein said byproduct is comprised of whole stillage.

17. The method of using a byproduct from a production of ethanol of claim 10, wherein said byproduct is comprised of thin stillage solubles.

* * * * *